US005665731A

United States Patent [19]

Hennessey

[11] Patent Number: 5,665,731
[45] Date of Patent: Sep. 9, 1997

[54] METHOD AND COMPOSITION FOR TREATING WITH A VASODILATOR INFLAMMATION, BONE LOSS AND DETACHMENT OF TEETH AS ASSOCIATED WITH PERIODONTAL

[76] Inventor: Richard K. Hennessey, 803 Cottonwood Dr., Severna Park, Md. 21146

[21] Appl. No.: 472,976

[22] Filed: Jun. 7, 1995

[51] Int. Cl.$^6$ .............. A61K 7/22; A61K 31/47; A61K 31/485
[52] U.S. Cl. .............. 514/307; 424/49; 424/54
[58] Field of Search .............. 424/49–58; 514/307

[56] References Cited

U.S. PATENT DOCUMENTS

| | | | |
|---|---|---|---|
| 2,507,086 | 5/1950 | Baizer | 260/285 |
| 3,823,234 | 7/1974 | Mauvernay | 424/180 |
| 3,832,460 | 8/1974 | Kosti | 424/54 |
| 3,910,921 | 10/1975 | Esanu | 260/286 |
| 4,018,927 | 4/1977 | Voorhees | 424/260 |
| 4,055,648 | 10/1977 | Sache | 424/260 |
| 4,089,943 | 5/1978 | Roberts et al. | 424/49 |
| 4,136,173 | 1/1979 | Pramoda et al. | 424/177 |
| 4,440,777 | 4/1984 | Zupan | 424/274 |
| 4,529,584 | 7/1985 | Mulvey et al. | 424/52 |
| 4,529,585 | 7/1985 | Hayes | 424/52 |
| 4,758,433 | 7/1988 | Johnson et al. | 424/195.1 |
| 4,801,587 | 1/1989 | Voss et al. | 514/307 |
| 5,059,603 | 10/1991 | Rubin | 514/264 |
| 5,278,172 | 1/1994 | Hennessey | 514/307 |
| 5,487,897 | 1/1996 | Polson et al. | 424/426 |

OTHER PUBLICATIONS

Batterman et al., CA74(1):2610a (Chemical Abstracts) 1970.
Matveikov et al., 89:185149 Biosis, BA87:96415, 1988.
Rusin et al., "Papaverine and Ro 20–1724 Inhibit Cyclic Nucleotide Phosphodiesterase Activity and Increase Cyclic AMP Levels in Psoriatic Epidermis in Vitro", *J. Invest. Derm.*, 71: 154–156 (1978).
Batterman et al., Angiology 21(9), pp. 612–626, 1970.
"Advances in Dentistry", John Hopkins Medical Letter, 4–6 (Jul. 1993).

*Primary Examiner*—Shep K. Rose
*Attorney, Agent, or Firm*—Foley & Lardner

[57] ABSTRACT

A process is provided which is useful in alleviating inflammation of gums, bone loss and detachment of teeth in a patient in need of such treatment. The process comprises administering a vasodilator to the inflamed gum tissue and other affected tissue, either topically or by injection. Advantageously, the vasodilator is papaverine or a pharmaceutically acceptable salt thereof such as papaverine hydrochloride. Advantageously, the papaverine hydrochloride may be administered topically in a composition comprising a carrier such as an aqua based transparent gel dental vehicle. The carrier dissolves the papaverine hydrochloride and enables it to penetrate the soft tissue of the gums and be absorbed into the inflamed tissue.

7 Claims, No Drawings

METHOD AND COMPOSITION FOR TREATING WITH A VASODILATOR INFLAMMATION, BONE LOSS AND DETACHMENT OF TEETH AS ASSOCIATED WITH PERIODONTAL

FIELD OF THE INVENTION

This invention relates to methods of treating inflammation of gums, bone loss and detachment of teeth in a patient in need of such treatment. The process comprises administering a vasodilator to the inflamed gum tissue, either topically or by injection. This invention also relates to methods of treating inflammation of such tissue by administering a composition comprising papaverine or a pharmaceutically acceptable salt thereof to the affected tissue.

BACKGROUND OF THE INVENTION

Periodontal disease is characterized by gingival inflammation and swelling of soft gum tissue, loss of bone structure and attachment loss of the affected teeth. The pockets caused by loss of bone are areas of maximum bacteria attack and gum inflammation both of which increases bone loss and destroys the micro ligaments that attach the teeth in the bone sockets.

There currently are many accepted methods of treatment for this ailment, including bactericides added to toothpaste, mouth washes, STIM-U-DENT™ stimulation with baking soda, and other anti-inflammatory preparations. In some cases, surgery of the diseased soft tissue is required. If the disease progresses to the extent that surgery is required, however, the treatment may not be effective enough to prevent future tooth loss.

While such periodontal disease can be treated by medication and surgery, albeit in some instances with limited success, there remains a need for additional methods for treatment.

SUMMARY OF THE INVENTION

Accordingly, it is an object of this invention to provide a method for the treatment of periodontal disease, more specifically, inflammation of gums, bone loss and detachment of teeth in a patient in need of such treatment.

It is a further object of this invention to provide a method for the treatment of such inflammation by topical administration of a composition to the inflamed tissue and surrounding area.

In accordance with one aspect of this invention, there is provided a process for treating such inflammation comprising the topical administration of a composition comprising a therapeutically effective amount of a vasodilator or salt thereof in a pharmaceutically acceptable carrier which dissolves the vasodilator and enables the vasodilator to penetrate the affected tissues.

There also are provided compositions for carrying out the foregoing processes.

In a preferred embodiment of the process and composition of this invention, the vasodilator comprises papaverine or a pharmaceutically acceptable salt thereof such as papaverine hydrochloride.

In another preferred embodiment, the papaverine or salt thereof is in a composition with a pharmaceutically acceptable carrier which dissolves the papaverine and enables the papaverine to penetrate the affected tissues.

Additional objects and advantages of the invention will be set forth in part in the description that follows, and in part will be obvious from the description, or may be learned by practice of the invention. The objects and advantages may be realized and obtained by means of the processes and compositions particularly pointed out in the appended claims.

DETAILED DESCRIPTION OF THE PREFERRED EMBODIMENTS

It has been discovered that administering a vasodilator or pharmaceutically acceptable salt thereof to the inflamed gums and surrounding tissue can reduce the inflammation of that tissue. Such inflammation is commonly associated with periodontal disease. Further, it has been discovered that, to be effective, the vasodilator or salt thereof either must be capable of penetrating the gum tissue so that its action is continuous over an extended period of time, or must be dissolved in a carrier which enables the vasodilator to be absorbed into the affected tissues. Alternatively, the vasodilator, with or without a pharmaceutically acceptable carrier, can be delivered directly to the inflamed tissue or surrounding area through injection (intradermally or subcutaneously), or by surgical means.

Vasodilators which can be used in accordance with this invention include, for example, ethaverine and salts thereof, totazoline and salts thereof, nylidin and salts thereof, diazaxide, minoxidil and papaverine, which is readily available in the hydrochloride form. The foregoing are only exemplary and many other vasodilators useful in this invention will be readily apparent to those skilled in the art.

To be effective, the vasodilator must reach the inflamed tissues. Thus, where topical administration is employed, the vasodilator must be able to penetrate the inflamed tissues. In cases where the vasodilator itself is incapable of such penetration and absorption, a topical-use carrier that both dissolves the vasodilator and facilitates its penetration through the affected tissues is required.

Suitable topical compositions thus include those pharmaceutical forms in which the compound is applied externally by direct contact with the inflamed tissue and surrounding tissue. Conventional pharmaceutical forms for this purpose include toothpastes, pastes, waxes, and the like. Preferably, the vasodilator will be completely solubilized in the composition so that it will be completely absorbed into the affected tissue.

The quantity of vasodilator administered can depend upon several factors including, inter alia, (1) the particular vasodilator used, e.g., its ability to penetrate the affected tissue, and the nature and magnitude of its effect on the tissue, (2) the method of administration, e.g., topical versus injection, (3) the carrier, and the solubility of the vasodilator in the carrier, (4) the individual requirements of the patient, and (5) possible side effects of the vasodilator. Those skilled in the art will be able to determine through the exercise of routine skill the amount of vasodilator to administer. It is contemplated that concentrations of vasodilator in topical compositions will range from less than one percent to a few percent (e.g., from about two to about four percent), to higher concentrations of five, ten, twenty or more percent by weight, especially when injectable compositions are used. Indeed, those skilled in the art may recognize vasodilators which can be administered topically or by injection without carriers, i.e., at full strength.

The topical composition so produced can be administered by brushing or massaging at least once per day, preferably twice daily and one application by massaging with one's finger between brushings. The excess toothpaste should be expectorated along with saliva from the mouth. For best results, however, the mouth should not be rinsed after the brushing or massage application for the first thirty days of treatment. Alternatively, the application may be repeated as necessary, up to several times per day, depending upon the concentration of vasodilator used and the other factor described above.

In a particularly preferred embodiment of this invention, the vasodilator comprises papaverine. Papaverine is a known alkaloid of chemical formula $C_{20}H_{21}NO_4$. It is readily available in hydrochloride form from Recordati Corp., Allendale, N.J. Taken orally, papaverine hydrochloride has proven useful in the treatment of migraine headaches. When applied topically, it also is useful for treating proliferating skin diseases (see, e.g., U.S. Pat. No. 4,098,127 to Voorhees). It has been used to improve the effectiveness of vein grafting procedures, and recent research suggests that it may be useful as an anti-retroviral agent. Although the preferred embodiment comprises the hydrochloride salt of papaverine, other salts or active forms of papaverine are contemplated and will be readily apparent to those skilled in the art.

In the case of papaverine hydrochloride, acceptable results are obtained with compositions comprising up to about 5% or more by weight of papaverine hydrochloride. Using the preferred carrier described below, particularly advantageous results have been obtained with compositions comprising from about 0.5% to about 2.0% by weight of papaverine hydrochloride. It has been found that the solubility and stability of papaverine hydrochloride can be a limiting factor in terms of the practical maximum weight percent of the papaverine hydrochloride in a topical composition. That is, the solubility of a stable formulation of papaverine hydrochloride in an aqueous-based carrier has been empirically determined to be about two percent. While higher percentages, e.g., up to about five percent, are possible, it has been found that the papaverine hydrochloride will begin to crystallize out of solution over time when higher concentrations are used. Thus, better stability is achieved with aqueous-based formulations when amounts of from about 0.5% to about 2.0% by weight of papaverine hydrochloride are used. Of course, those skilled in the art may recognize other types of topical formulations or processes for formulation which will enable relatively stable compositions having higher weight percentages of papaverine hydrochloride, and such compositions are clearly contemplated in this invention.

A water soluble vasodilator such as a papaverine hydrochloride has advantages in that it is readily absorbed by the gum tissues. Papaverine hydrochloride is 2% soluble in water or aqueous based gel dental vehicles.

In one advantageous embodiment, 2 parts of the vasodilator are blended with 98 parts of a transparent dental gel vehicle having the following formulation

| | |
|---|---|
| Glycerine | 10% |
| Sorbitol solution (70%) | 75% |
| Sodium benzoate | 0.5% |
| Sodium Carboxymethyl cellulose | 2.0% |
| Sodium lauryl sulfate | 1.5% |
| Flavor | 0.8% |
| Ethanol (95%) | 10.0% |
| Color (Red) | 0.10% |

Toothpaste other than the above described gel may be used as the vehicle for the vasodilator providing sufficient water is present in the formula to dissolve the vasodilator, papaverine hydrochloride, or comparable substitute. Additionally 3 to 10% of distilled water may be added to the mixture to increase the solubility of the papaverine hydrochloride and/or, correct the viscosity of the final composition.

While not wishing to be bound by any particular theory, it is believed that the vasodilator effects the relaxation of the smooth muscles of both the arterial and venous blood vessels, which allows the vessels to dilate and increase the flow of blood through the inflamed tissues. The observed absence of edema of the gums after treatment with papaverine hydrochloride attests to the increase in venous blood flow. Since the body's immune system is carried by the blood, additional flow also increases the immune cells passing through the diseased tissues. Also, any refuse from cell action is removed through the venous system. This constant flow of pure blood through the area also could explain the decrease in bacterial action in the inflamed gum tissues.

The following examples are intended solely to illustrate the invention, and do not limit the invention in any way.

EXAMPLE 1

A composition was prepared using papaverine hydrochloride available from Recordati Corp., Allendale, N.J. and a suitable carrier. The carrier was clear gel toothpaste as manufactured by Colgate-Palmolive Company of New York, N.Y.

Two grams of papaverine hydrochloride were thoroughly mixed with 98 grams of the clear gel toothpaste and allowed to stand for 24 hours. The mixture was then mixed again and was observed for undissolved papaverine hydrochloride salt crystals. Additionally, 5 ml. of distilled water was added to the mixture to reduce the viscosity and increase the solubility of the remaining solids. This mixture was thoroughly mixed several times over a 72 hour period. This toothpaste gel mixture was now ready for brushing and massaging of the gum surfaces.

EXAMPLE 2

In April 1989, a male dental patient was informed that he had extensive bone loss on both upper and lower teeth. Deep pockets were found between the teeth and these pockets were deepening upon each 6 month examination. The patient told the dentist that he wished to save his remaining teeth if possible. The dentist recommended daily massaging with STIM-U-DENT™ and baking soda. One year later the patient had to have two molars extracted because of a lack of attachment and infection. Total extractions from periodontal disease to date amount to eight molars. In January 1992, the dentist discontinued the daily massaging with STIM-U-DENT™ and baking soda and began testing anti-inflammatory medication in toothpaste gel using the composition referred to in Example 1. The patient brushed his teeth thoroughly twice daily and applied medication once by finger in between brushings. In January 1993, a semi-annual inspection showed considerable improvement in soft tissue. By January 1994, the teeth were firmly attached in their sockets and the soft tissue appeared healthy.

Eliminating the inflammation within the pocket areas created by the disease allowed the gums to heal. Micro ligaments filled the void between teeth and bone, reattaching the teeth firmly into their sockets and eliminating the pocket areas of bacterial activity.

It will be apparent to those skilled in the art that various modifications and variations can be made to the compositions of matter and processes of this invention. Thus, it is intended that the present invention cover the modifications and variations of this invention provided they come within the scope of the appended claims and their equivalents. All references in the claims to a composition of matter such as a vasodilator or papaverine, whether in general or by name, expressly include the salts and hydrates thereof.

What is claimed is:

1. A process for treating inflammation of gums, bone loss and detachment of teeth in a patient in need of such treatment, comprising topically or by injection administering to an external area near the inflamed gum, bone or teeth an effective amount of a composition comprising:
   (a) a therapeutically effective amount of an active ingredient comprising papaverine or a pharmaceutically acceptable salt thereof; and
   (b) a carrier for the topical administration of said active ingredient, wherein
   said active ingredient is at least partially soluble in said carrier, and said carrier enables the penetration of the active ingredient through the gums and absorption of said active ingredient into the inflamed tissue.

2. A process according to claim 1, wherein said active ingredient comprises papaverine hydrochloride.

3. A process according to claim 2, wherein said composition comprises up to about 5% by weight of papaverine hydrochloride.

4. A process according to claim 2, wherein said composition comprises from about 0.5% to about 2.0% by weight of papaverine hydrochloride.

5. A process according to claim 1, wherein said carrier predominantly comprises water.

6. A process according to claim 4, wherein said carrier predominantly comprises water.

7. A process according to claim 1, wherein said step of administering is carried out at least once per day.

* * * * *